(12) United States Patent
Motohara et al.

(10) Patent No.: US 10,610,090 B2
(45) Date of Patent: Apr. 7, 2020

(54) ELECTRONIC CIRCUIT UNIT, IMAGING UNIT, IMAGING MODULE, AND ENDOSCOPE

(71) Applicant: OLYMPUS CORPORATION, Tokyo (JP)

(72) Inventors: Hiroyuki Motohara, Hachioji (JP); Kazuki Kawachi, Yokohama (JP)

(73) Assignee: Olympus Corporation, Tokyo (JP)

( * ) Notice: Subject to any disclaimer, the term of this patent is extended or adjusted under 35 U.S.C. 154(b) by 2 days.

(21) Appl. No.: 16/158,516

(22) Filed: Oct. 12, 2018

(65) Prior Publication Data

US 2019/0038117 A1 Feb. 7, 2019

Related U.S. Application Data

(63) Continuation of application No. PCT/JP2017/016560, filed on Apr. 26, 2017.

(30) Foreign Application Priority Data

May 10, 2016 (JP) ................................. 2016-094727

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00124* (2013.01); *G02B 23/24* (2013.01); *H01L 23/12* (2013.01);
(Continued)

(58) Field of Classification Search
None
See application file for complete search history.

(56) References Cited

U.S. PATENT DOCUMENTS 9,325,881 B2 4/2016 Zen
2006/0109368 A1 5/2006 Ayrenschmalz

FOREIGN PATENT DOCUMENTS

JP 2006-023776 A 1/2006
JP 2006-025852 A 2/2006
(Continued)

OTHER PUBLICATIONS

International Search Report dated Jul. 4, 2017 issued in PCT/2017/016560.
(Continued)

*Primary Examiner* — Dimary S Lopez Cruz
(74) *Attorney, Agent, or Firm* — Scully, Scott, Murphy & Presser PC

(57) ABSTRACT

A disclosed electronic circuit unit includes a first circuit board in which first electrode pads, mounting lands and second electrode pads are formed and that has vias and wirings; a second circuit board in which third electrode pads and dummy pads are formed and that has vias and wirings; and electronic components that are connected to the mounting lands. When the dummy pads are projected in the direction orthogonal to a surface, one of the dummy pads is overlapped one of electrodes of one of the electronic components. The mounting lands for the electronic components overlapping the dummy pads at the time of the projection are connected to, by connecting members, the second electrode pads, the wirings, and the like, the dummy pads connected to the third electrode pads by the wirings or the like.

9 Claims, 10 Drawing Sheets

(51) Int. Cl.
*H05K 1/18* (2006.01)
*H04N 5/225* (2006.01)
*H01L 23/12* (2006.01)
*G02B 23/24* (2006.01)
*H05K 1/14* (2006.01)

(52) U.S. Cl.
CPC ........... *H04N 5/225* (2013.01); *H04N 5/2253* (2013.01); *H05K 1/14* (2013.01); *H05K 1/18* (2013.01)

(56) References Cited

FOREIGN PATENT DOCUMENTS

| | | |
|---|---|---|
| JP | 2006-174431 A | 6/2006 |
| JP | 2013-135823 A | 7/2013 |
| JP | 2014-000314 A | 1/2014 |
| JP | 2015-060947 A | 3/2015 |
| JP | 2015-173736 A | 10/2015 |

OTHER PUBLICATIONS

Japanese Decision of a Patent Grant dated Jan. 16, 2018 issued in JP 2017-554530.

ELECTRONIC CIRCUIT UNIT, IMAGING UNIT, IMAGING MODULE, AND ENDOSCOPE

CROSS-REFERENCE TO RELATED APPLICATION(S)

This application is a continuation of International Application No. PCT/JP2017/016560, filed on Apr. 26, 2017 which claims the benefit of priority of the prior Japanese Patent Application No. 2016-094727, filed on May 10, 2016, the entire contents of which are incorporated herein by reference.

BACKGROUND

The present disclosure relates to an electronic circuit unit, an imaging unit, an imaging module, and an endoscope.

In the past, endoscopes that are inserted into subjects for observation of sites to be examined have been known and widely used in, for example, the medical field. This type of endoscope is constituted by having built-in an imaging module including an electronic circuit unit in which an electronic component, such as an image sensor, is mounted on the distal end portion of a flexible and elongated insertion tool. In order to reduce a load applied to a subject, it is desired to reduce a diameter, a length, and a size of the distal end portion of the insertion tool.

Various kinds of electronic circuit units formed by laminating circuit boards have been proposed while improving packaging density by forming finer connection pitches and by reducing mounting spaces of adjacent electronic components on a flat electronic circuit board (for example, see Japanese Laid-open Patent Publications No. 2015-60947 and No. 2006-23776).

SUMMARY

The present disclosure has been conceived in light of the circumstances described above, and is directed to an electronic circuit unit, an imaging unit, an imaging module, and an endoscope that can prevent a failure due to short circuits occurring between components while reducing their size.

According to a first aspect of the present disclosure, an electronic circuit unit is provided which includes a first circuit board in which a plurality of first electrode pads are formed on a front surface and a plurality of mounting lands and a plurality of second electrode pads are formed on a back surface, the first circuit board including a plurality of vias and wirings; a second circuit board in which two dummy pads and a plurality of third electrode pads that are connected to corresponding ones of the second electrode pads on the first circuit board via connecting members are formed on a front surface and that has a plurality of vias and wirings; and a plurality of electronic components that are connected to the mounting lands, wherein when the dummy pads are projected in the direction orthogonal to a connecting surface between the first circuit board and the second circuit board, at least part of the dummy pads overlaps at least part of electrodes of one of the plurality of electronic components, and the mounting lands for the electronic components overlapped with the at least part of the dummy pads due to the projection are connected to the dummy pads through a predetermined path, wherein the predetermined path includes the vias and the wirings of the first circuit board that connect the mounting lands and the second electrode pads, the vias and the wirings of the second circuit board that connect the third electrode pads and the dummy pads, and the connecting member that connects the second electrode pad and the third electrode pad.

According to a second aspect of the present disclosure, an imaging unit is provided which includes an electronic circuit unit according to the first aspect; and a semiconductor package that has an image sensor provided on a front surface, and sensor electrodes formed on a back surface, wherein first electrode pads included in the electronic circuit unit are connected to the respective sensor electrodes included in the semiconductor package via connecting members, and the electronic circuit unit is located within a plane of projection of the semiconductor package in the optical axis direction.

According to a third aspect of the present disclosure, an imaging module is provided which includes an electronic circuit unit according to the first aspect; a semiconductor package that has an image sensor provided on a front surface, and electrodes formed on a back surface; and a plurality of cables, wherein cable connection electrodes are formed on two opposing side surfaces of the second circuit board in the electronic circuit unit and the plurality of cables are connected to corresponding one of the cable connection electrodes, first electrode pads included in the electronic circuit unit are connected to the respective sensor electrodes included in the semiconductor package via connecting members, and the electronic circuit unit and the plurality of cables are located within a plane of projection of the semiconductor package in the optical axis direction.

According to a fourth aspect of the present disclosure, an endoscope is provided which includes an insertion portion in which an imaging unit according to the third aspect is provided at a distal end.

DETAILED DESCRIPTION

Figure 1:
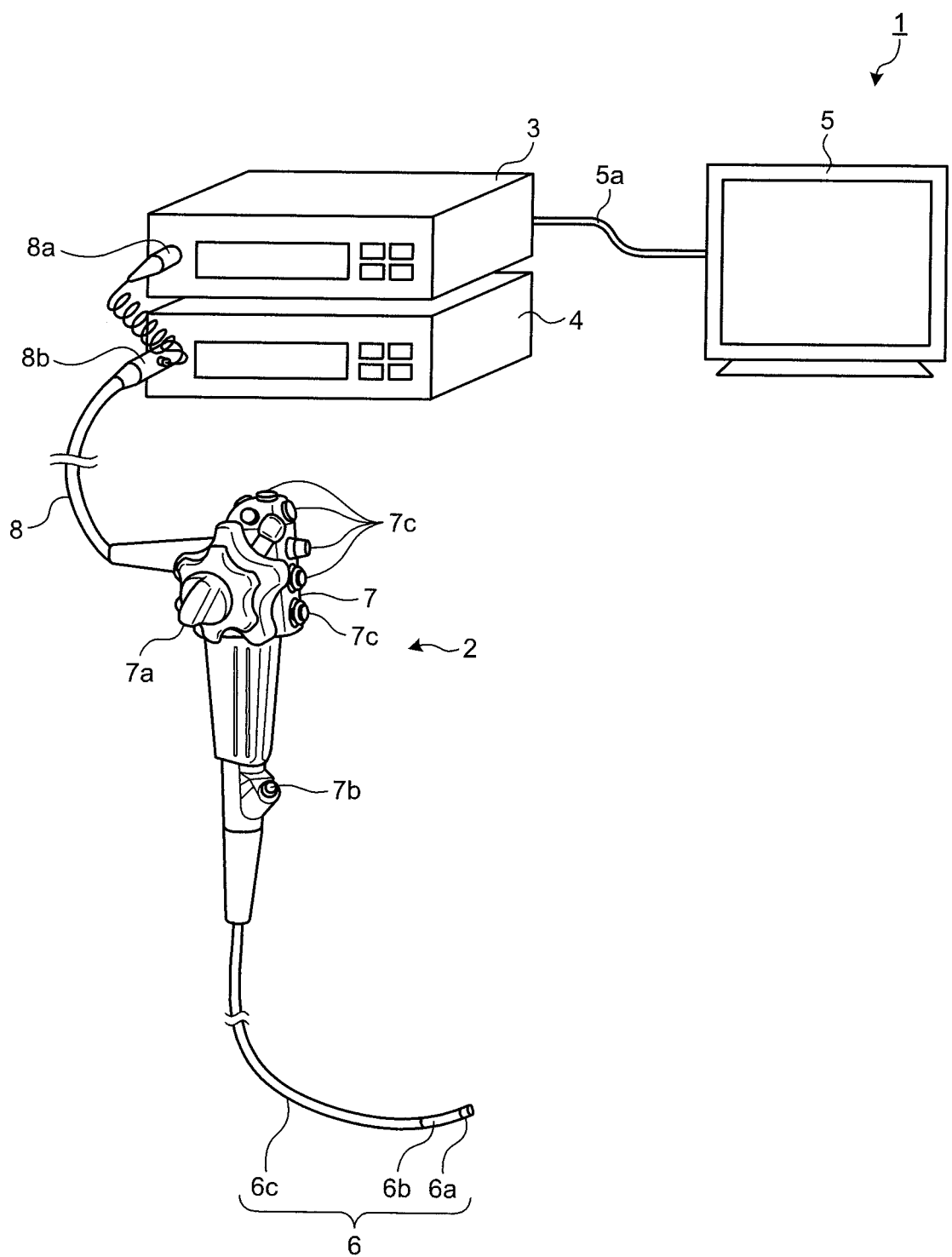
FIG. 1 is a diagram schematically illustrating an overall configuration of an endoscope system according to an embodiment of the present disclosure.

In the following, as modes for carrying out the present disclosure (hereinafter, referred to as "embodiments"), an endoscope system provided with an imaging unit will be described. The present disclosure is not limited to the embodiments. In the drawings, components that are identical to those in embodiments are assigned the same reference numerals. The drawings used for the descriptions below are only schematic illustrations. The relationship between the thickness and the width of each member, the proportions of each member, and so on are different from those used in practice. The size or reduction in scale of elements may sometimes differ between the drawings.

Embodiment

FIG. 1 is a diagram schematically illustrating an overall configuration of an endoscope system 1 according to an embodiment of the present disclosure. As illustrated in FIG. 1, the endoscope system 1 according to an embodiment includes an endoscope 2 that is inserted into a subject, that captures an image of an inside of the subject, and that generates an image signal of the inside of the subject; an information processing apparatus 3 that performs predetermined image processing on the image signal generated by the endoscope 2 and that controls each unit included in the endoscope system 1; a light source device 4 that generates illumination light of the endoscope 2; and a display device 5 that displays an image of the image signal that has been subjected to image processing performed by the information processing apparatus 3.

The endoscope 2 includes an insertion portion 6 that is inserted into the subject, an operating unit 7 that is on the proximal end portion side of the insertion portion 6 and that is held by an operator; and a flexible universal cord 8 extending from the operating unit 7.

The insertion portion 6 is implemented by using a lighting fiber (light guide cable), an electricity cable, an optical fiber, or the like. The insertion portion 6 includes a distal end portion 6a that is provided with a built-in imaging unit, which will be described later; a bending portion 6b that is freely bendable formed by a plurality of bending sections, and a flexible tube portion 6c that is flexible and that is provided on the proximal end portion side of the bending portion 6b. The distal end portion 6a is provided with an illumination portion that illuminates inside the subject via an illumination lens, an observation portion that captures an image of an inside of the subject, an opening portion communicating with a treatment instrument purpose channel, and an air supply/water supply nozzle (not illustrated).

The operating unit 7 includes a bending knob 7a that bends the bending portion 6b in the vertical direction and the horizontal direction, a treatment instrument insertion portion 7b in which a treatment instrument, such as biological forceps or a laser scalpel, is inserted into the body cavity of the subject, and a plurality of switch units 7c that performs operation of peripheral equipment, such as the information processing apparatus 3, the light source device 4, an air supply device, a water supply device, and a gas supply device. The treatment instrument inserted from the treatment instrument insertion portion 7b comes out from the opening portion at the distal end of the insertion portion 6 via the treatment instrument purpose channel provided inside the insertion portion 6.

The universal cord 8 is constituted by using a lighting fiber, a cable, or the like. The universal cord 8 is branched at the proximal end. The end portion corresponding to one of the branched portions is a connector 8a, whereas the proximal end corresponding to the other one of the branched portions is a connector 8b. The connector 8a can be freely inserted to and removed from the connector of the information processing apparatus 3. The connector 8b can be freely inserted to and removed from the light source device 4. The universal cord 8 allows the illumination light emitted from the light source device 4 to propagate through the connector 8b and the lighting fiber to the distal end portion 6a. Furthermore, the universal cord 8 transmits the image signal captured by the imaging unit, which will be described later, to the information processing apparatus 3 through the cable and the connector 8a.

The information processing apparatus 3 performs predetermined image processing on the image signal output from the connector 8a and performs overall control of the endoscope system 1

The light source device 4 is constituted by using a light source that emits light, a condenser lens, or the like. The light source device 4 emits light from the light source under the control of the information processing apparatus 3 and supplies the light, as illumination light for illuminating an inside of the subject that is an object, to the endoscope 2 connected through the connector 8b and the lighting fiber of the universal cord 8.

The display device 5 is constituted by using a display using liquid crystal display or organic electro luminescence (EL). The display device 5 displays, through a video image cable 5a, various kinds of information including images that have been subjected to predetermined image processing performed by the information processing apparatus 3. Consequently, by operating the endoscope 2 while viewing an image (in-vivo image) displayed by the display device 5, an operator can observe a desired position of the subject and judge properties at the position.

Figure 2:
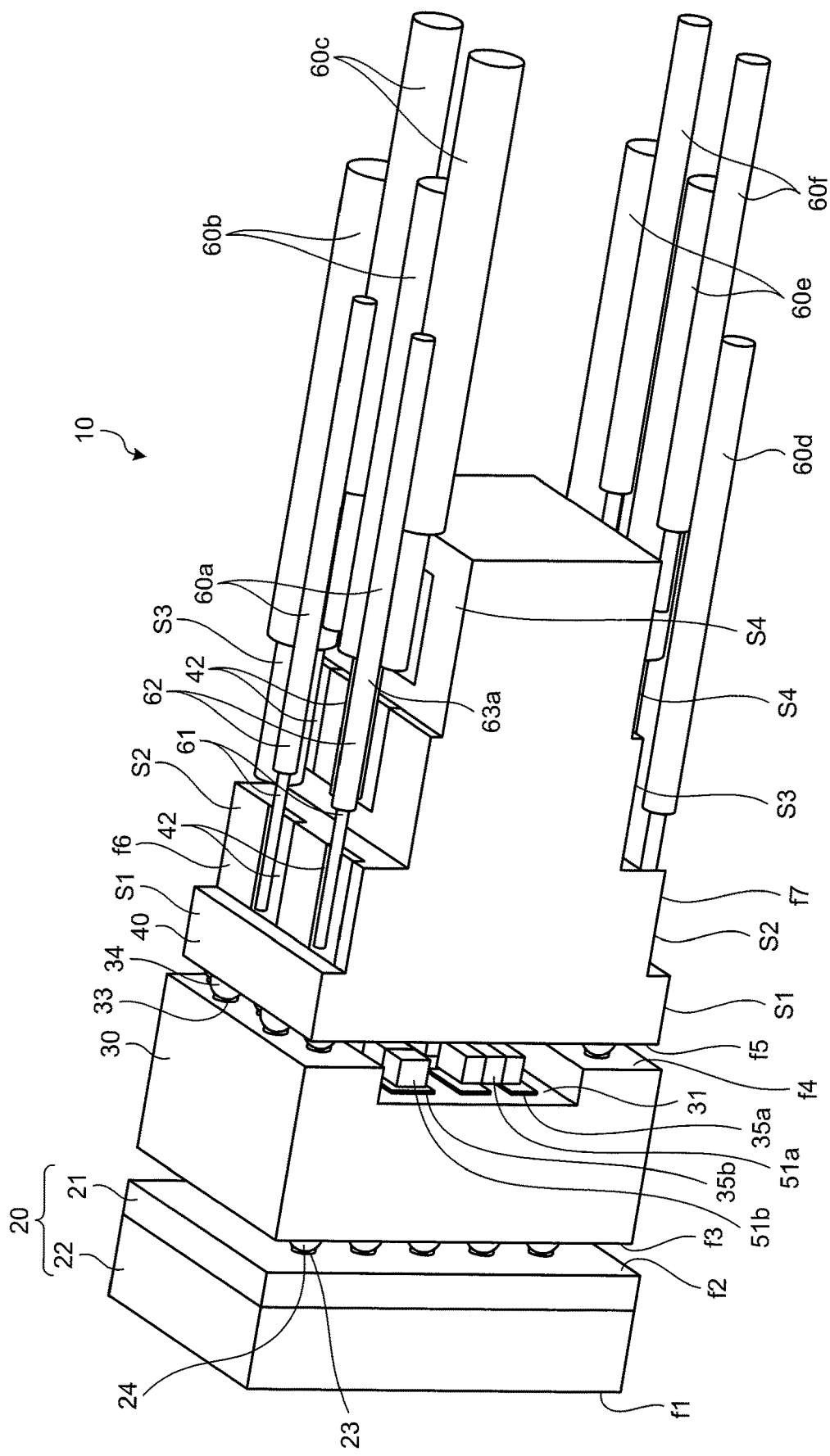
FIG. 2 is a perspective view of an imaging unit disposed at a distal end portion of an endoscope illustrated in FIG. 1.
Figure 3:
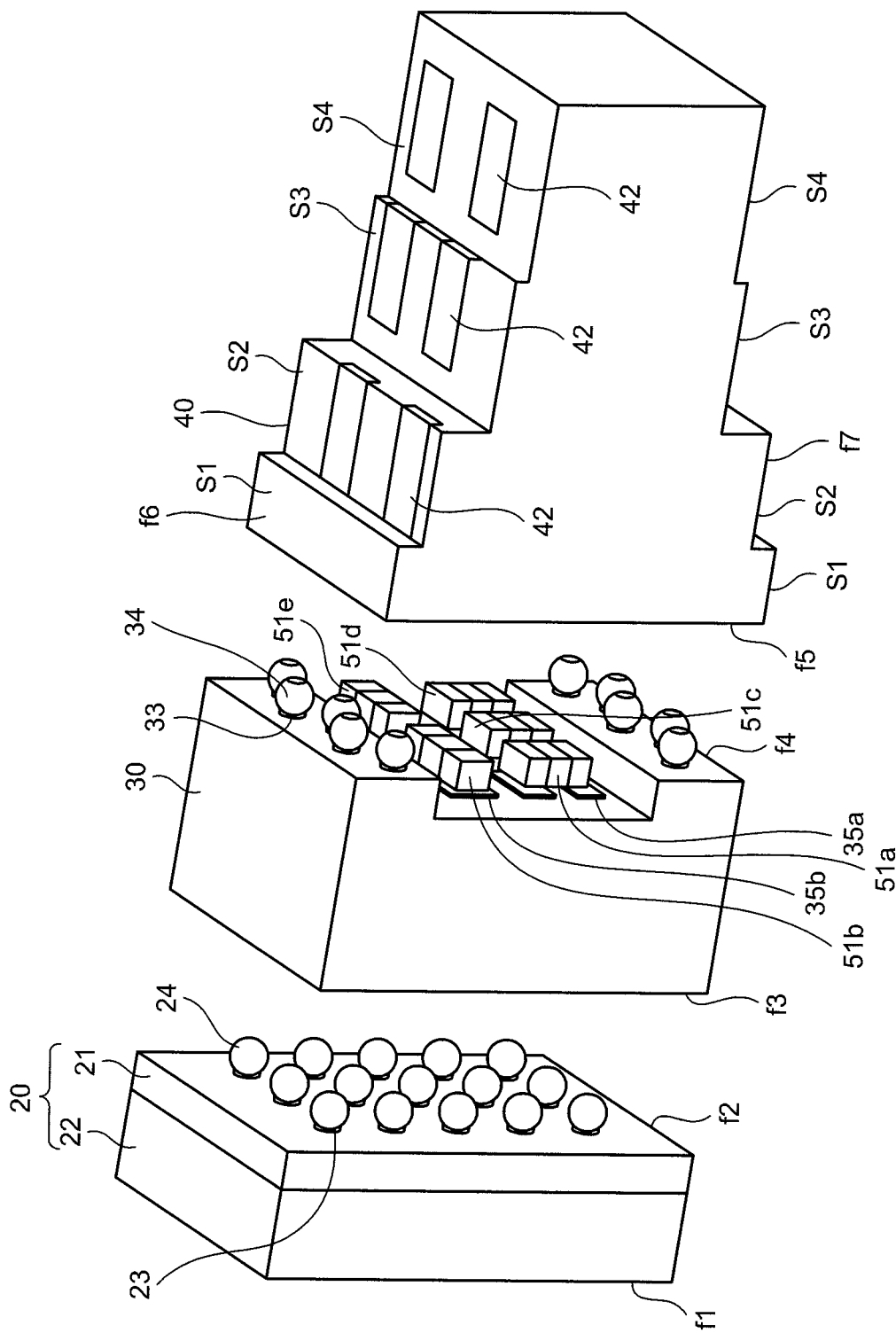
FIG. 3 is an exploded diagram of the imaging unit illustrated in FIG. 2.

In the following, the imaging unit used in the endoscope system 1 will be described in detail. FIG. 2 is a perspective view of an imaging unit 10 disposed at a distal end portion of the endoscope illustrated in FIG. 1. FIG. 3 is an exploded diagram of the imaging unit 10 illustrated in FIG. 2.

The imaging unit 10 includes a semiconductor package 20, a first circuit board 30, a second circuit board 40, electronic components 51a to 51e (51), and a plurality of cables 60a to 60f. The semiconductor package 20 has an image sensor, and sensor electrodes 23 formed on a surface f2 that is a back surface. The first circuit board 30 has first electrode pads 32 (see FIG. 6) and second electrode pads 33 formed on a surface f3 that is a front surface and on a surface f4 that is a back surface, respectively. The first electrode pads 32 on the surface f3 are electrically and mechanically connected to the sensor electrodes 23 on the semiconductor package 20. The second circuit board 40 has third electrode pads 41a to 41j (41) (see FIG. 5) formed on a surface f5 that is a front surface, and cable connection electrodes 42 formed on a surface f6 and a surface f7 that are side surfaces facing each other. The electronic components 51a to 51e (51) are mounted on the surface f4 that is a back surface of the first circuit board 30. The plurality of cables 60a to 60f are electrically and mechanically connected to corresponding ones of the cable connection electrodes 42 on the surface f6 and the surface f7 that are the side surfaces of the second circuit board 40.

In the imaging unit 10, the first circuit board 30, the second circuit board 40, and the plurality of cables 60a to 60f connected to corresponding ones of the cable connection electrodes 42 on the surface f6 and the surface f7 are accommodated within a shadow of the semiconductor package 20, the shadow being created by light incident toward a light-receiving surface of the semiconductor package 20 in a normal direction thereof.

The semiconductor package 20 has the structure in which glass 22 is bonded on an image sensor 21. Light collected by a lens unit is incident on the light-receiving surface of the image sensor 21 provided with a light-receiving unit through a surface f1 that is the front surface of the glass 22. On the surface f2 (back surface) of the image sensor 21, the sensor electrodes 23 and connecting members 24 formed of solder balls or the like are formed. The connecting members 24 may be metal core solder balls, resin core solder balls, Au bumps, or the like, rather than the solder balls. It is preferable that the semiconductor package 20 be a chip size package (CSP) into which the image sensor chips in a state of a wafer on which wirings, electrodes, and resin-sealing have been formed are diced so as to have the same size of the semiconductor package 20.

The first circuit board 30 has a plate shape formed by laminating a plurality of boards on which wirings have been arranged (plurality of boards parallel to the surface f3 and the surface f4 are laminated). For the laminated boards, ceramic substrates, glass epoxy boards, flexible substrates, glass substrates, silicon substrates are used. Inside the first circuit board 30, a plurality of vias are formed which allow the wirings on the laminated boards to be in electrical communication. The first electrode pads 32 are formed on the surface f3 of the first circuit board 30 and are electrically and mechanically connected to the sensor electrodes 23 on the semiconductor package 20 via the connecting members 24. The connecting portion between the first electrode pads 32 on the surface f3 and the sensor electrodes 23 on the surface f2 are sealed with a sealing resin (not illustrated).

Figure 4:
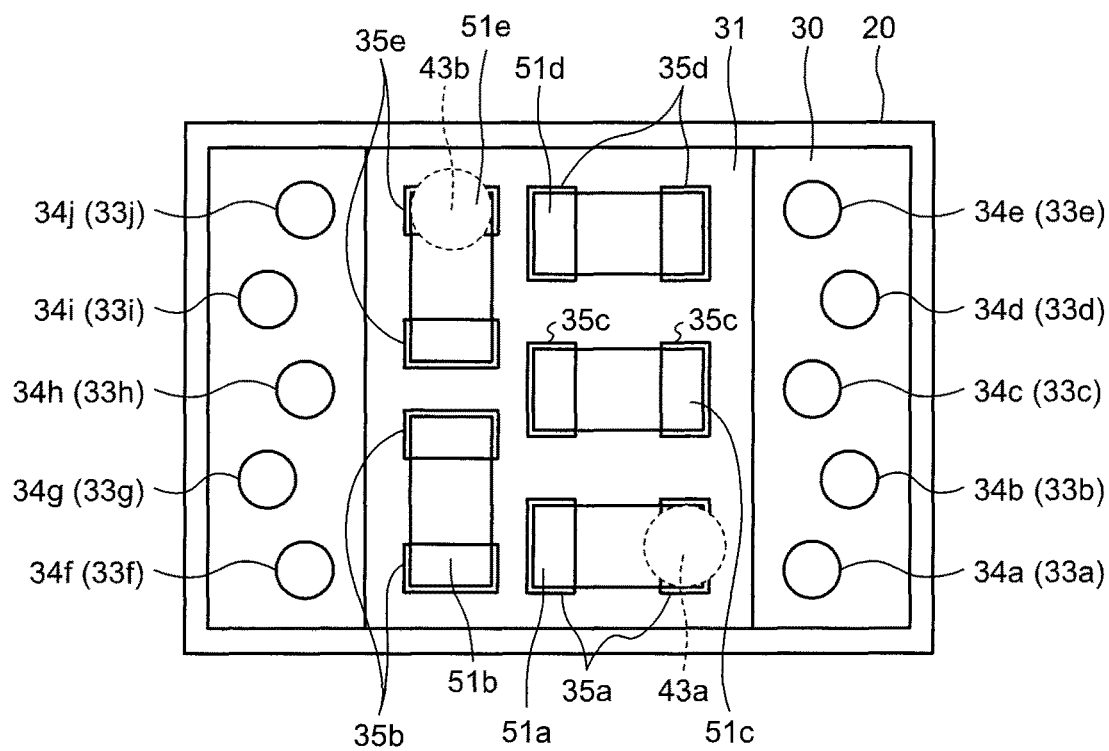
FIG. 4 is a plan view of a first circuit board on the back surface side.

Furthermore, as illustrated in FIG. 4, a concave portion 31 is provided at the center of the surface f4 of the first circuit board 30 and mounting lands 35a to 35e (35) on which the electronic components 51a to 51e are mounted are formed in the concave portion 31. Examples of the electronic components 51a to 51e to be mounted include passive components, such as condensers and resistance coils, and active components, such as driver ICs. By mounting the electronic components 51a to 51e in the concave portion 31 located around the center of the first circuit board 30, because the distance between the image sensor 21 and the electronic components 51a to 51e can be reduced, it is possible to decrease the impedance and stably drive the image sensor 21, thereby obtaining images with high quality. Furthermore, because the concave portion 31 is provided on the surface f4 of the first circuit board 30 and accommodates the electronic components 51a to 51e, it is possible to reduce the length of a hard portion (the length of the hard portion of the imaging unit 10 in the optical axis direction). Second electrode pads 33a to 33j are formed on the portion other than the concave portion 31 on the surface f4 of the first circuit board 30 and are electrically and mechanically connected to the third electrode pads 41a to 41j on the surface f5 of the second circuit board 40 via connecting members 34a to 34j. Examples of the connecting members 34 include solder balls, metal core solder balls, resin core solder balls, Au bumps, and the like.

The second circuit board 40 is formed of a ceramic substrate, a glass epoxy board, a glass substrate, a silicon substrate, or the like, is constructed by laminating a plurality of boards in which wirings have been arranged, and in which the opposing side surfaces of the surface f6 and the surface f7 have a step like shape.

Figure 5:
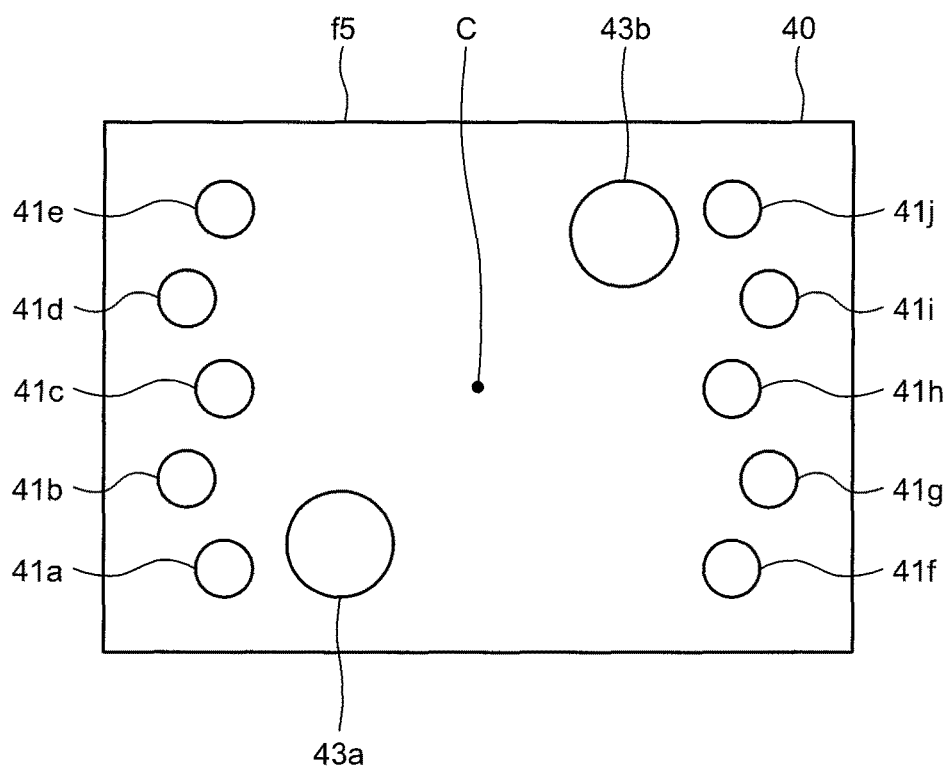
FIG. 5 is a plan view of a second circuit board on the front surface side.

As illustrated in FIG. 5, on the surface f5 that is the front surface of the second circuit board 40, the third electrode pads 41a to 41j connected to the second electrode pads 33a to 33j, respectively, and two dummy pads 43a and 43b are formed. The dummy pads 43a and 43b are formed by using the same process as that used for the second electrode pads 33a to 33j. The connecting portion between the second electrode pads 33a to 33j on the surface f4 and the third electrode pads 41a to 41j on the surface f5 and the inner portion of the concave portion 31 are sealed with a sealing resin (not illustrated). The dummy pads 43a and 43b are disposed so as to be rotationally symmetric with respect to the center C of the surface f5 that is the front surface of the second circuit board 40. Furthermore, FIG. 4 illustrates the dummy pads 43a and 43b by dotted lines at the position obtained when the dummy pads 43a and 43b are projected in the optical axis direction (the direction orthogonal to the surface f4 and the surface f5 that are the connecting surface between the first circuit board 30 and the second circuit board 40). The dummy pad 43a is disposed at the position overlapping the electrode located on the right side of the electronic component 51a in FIG. 4, whereas the dummy pad 43b is disposed at the position overlapping the electrode located on the upper side of the electronic component 51e in FIG. 4.

Each of the surface f6 and the surface f7 that are the side surfaces of the second circuit board 40 includes step portions S1, S2, S3, and S4. Distances between the step portions opposed each other become smaller in stages along a direction from the semiconductor package 20 to the second circuit board 40.

The cable connection electrodes 42 are formed on the step portions S2, S3, and S4 of the surface f6 and the surface f7. The cable connection electrodes 42 on the step portions S2, S3, and S4 are disposed so as to be deviated, without being overlapped with one another in the optical axis direction. The cables 60a to 60f (60) are cables having different outer diameters. An outer cover 62 of one end portion having insulation properties is peeled off and an exposed core wire 61 is electrically and mechanically connected to the cable connection electrode 42 with solder (not illustrated). By connecting the cables 60a and 60d having a small outer diameter to the cable connection electrodes 42 located at the step portion S2 on the distal end side and by connecting the cables 60c having a large outer diameter to the cable connection electrodes 42 located on the proximal end side, the cables 60a to 60f can be accommodated within the plane of projection of the semiconductor package 20 in the optical axis direction, thereby it is possible to reduce diameter size of the imaging unit 10.

Figure 6:
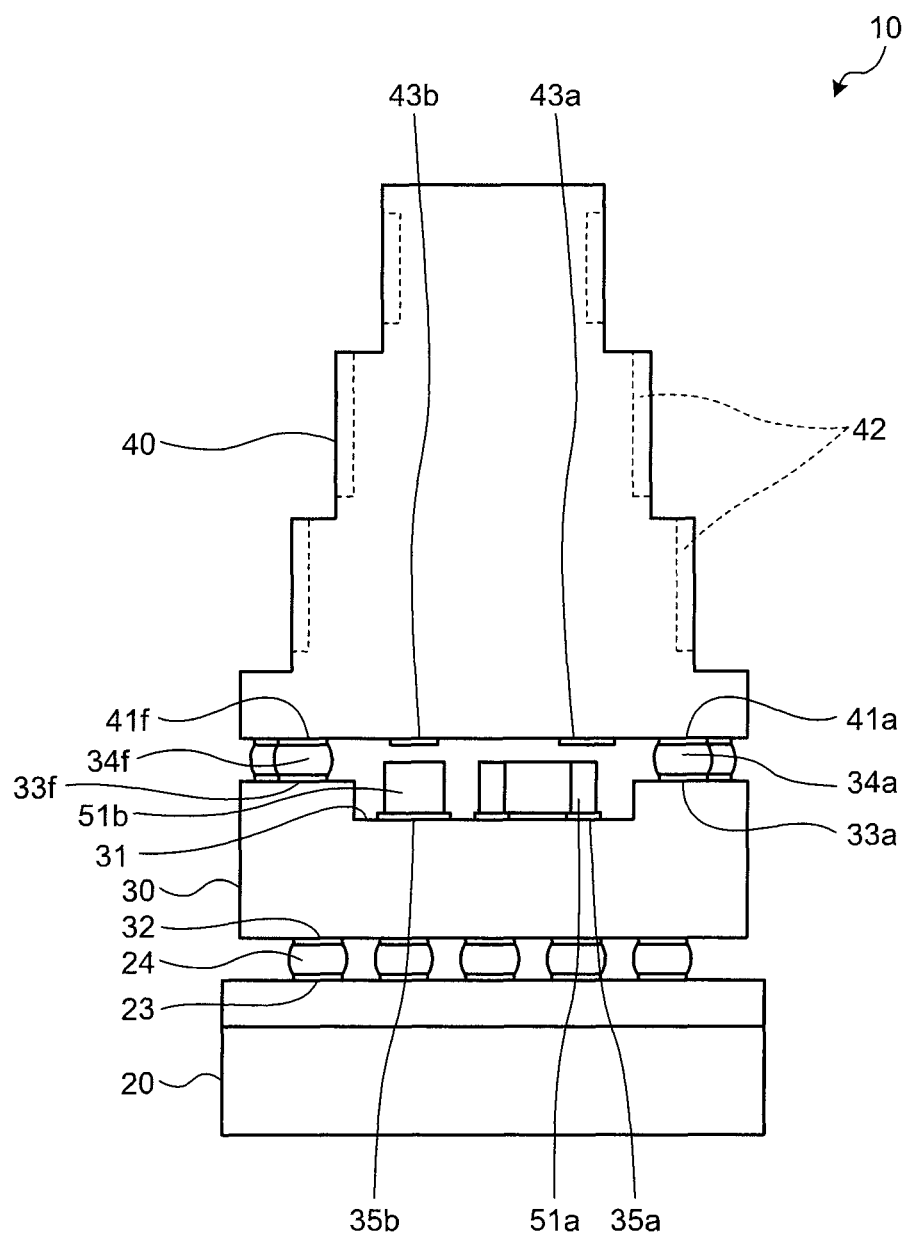
FIG. 6 is a side view of the imaging unit illustrated in FIG. 2.
Figure 7:
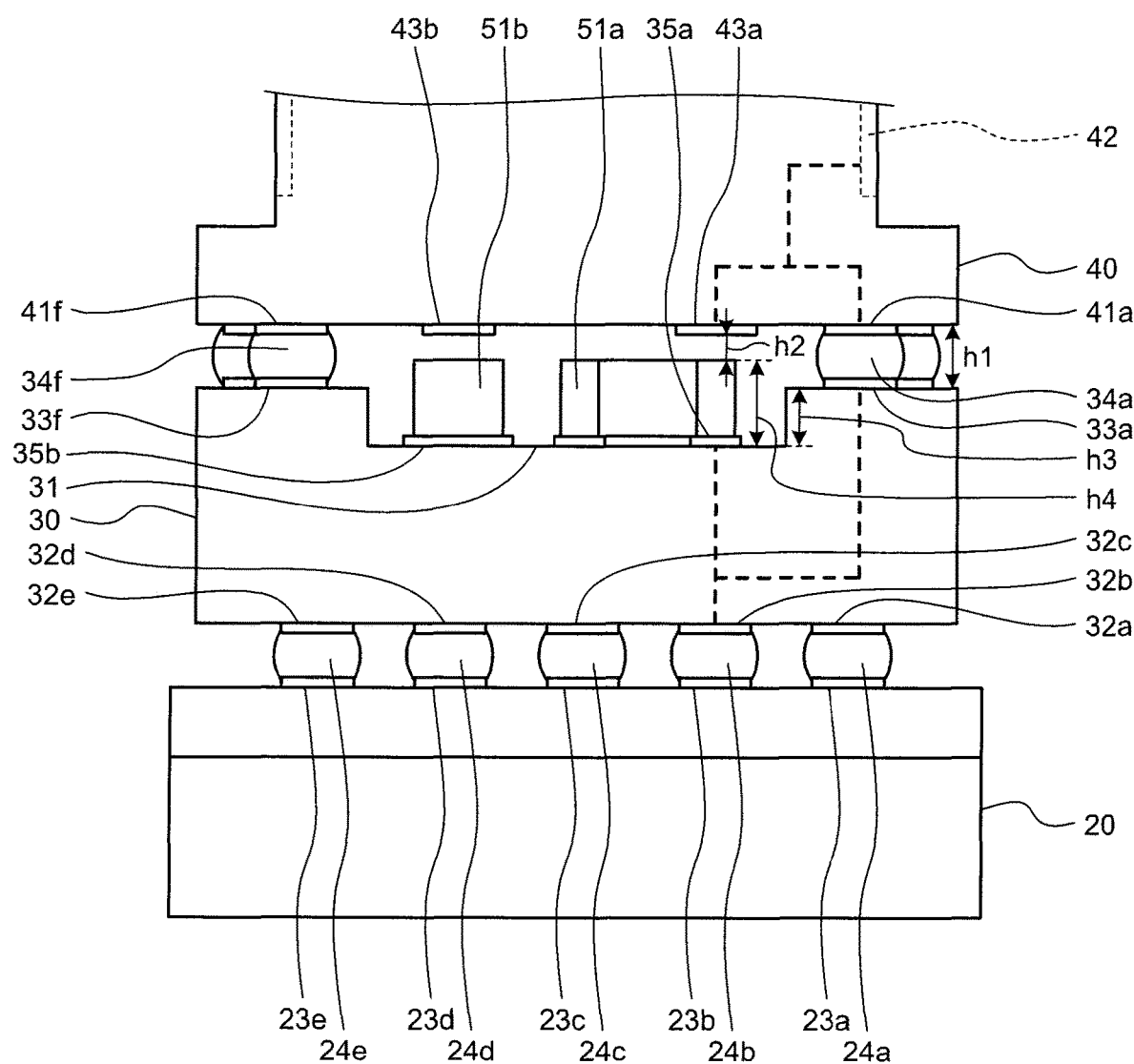
FIG. 7 is a partially enlarged view of the imaging unit illustrated in FIG. 6.
Figure 8:
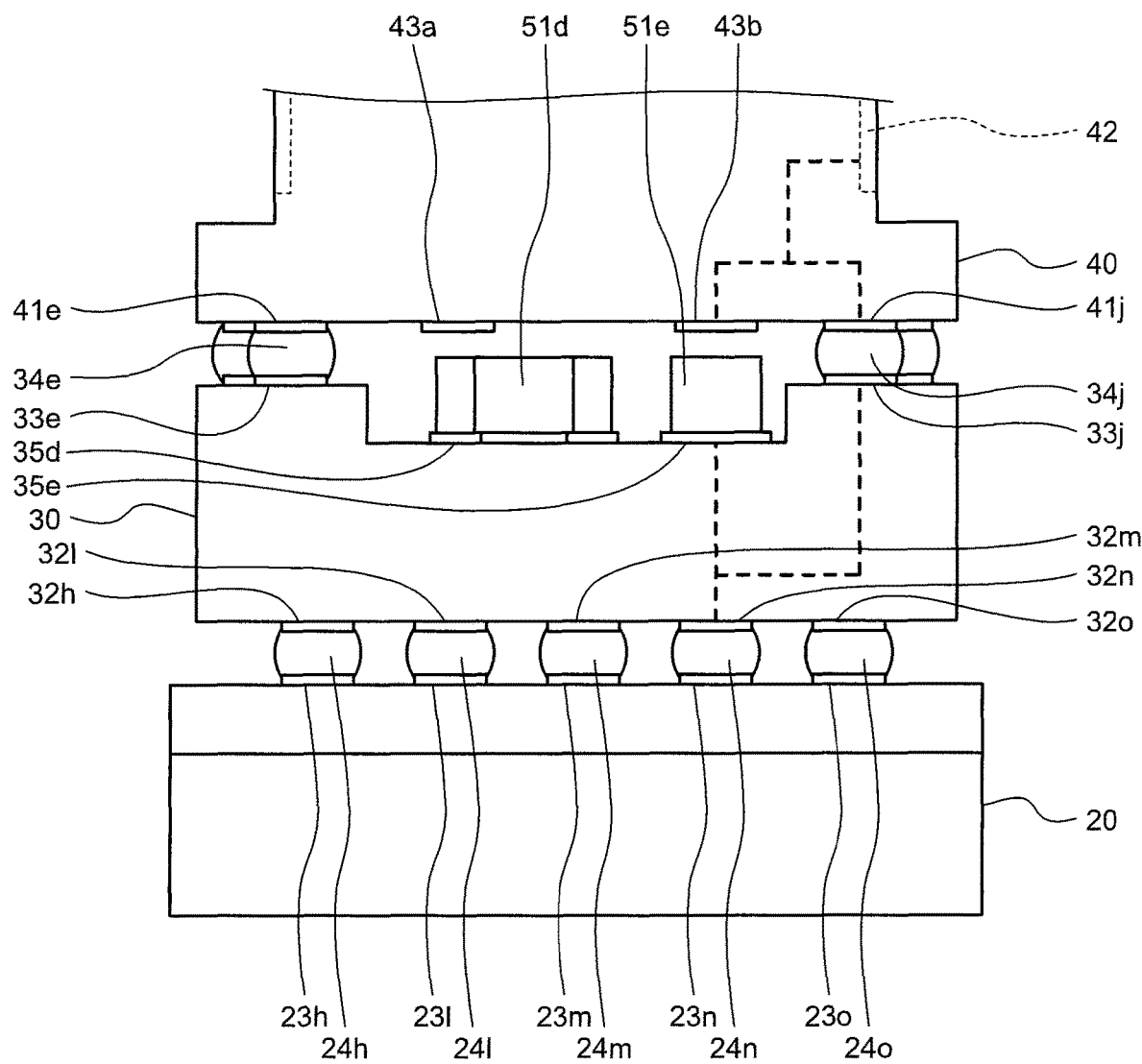
FIG. 8 is a partially enlarged view of the imaging unit taken from a side surface side opposing the surface illustrated in FIG. 7.
Figure 9:
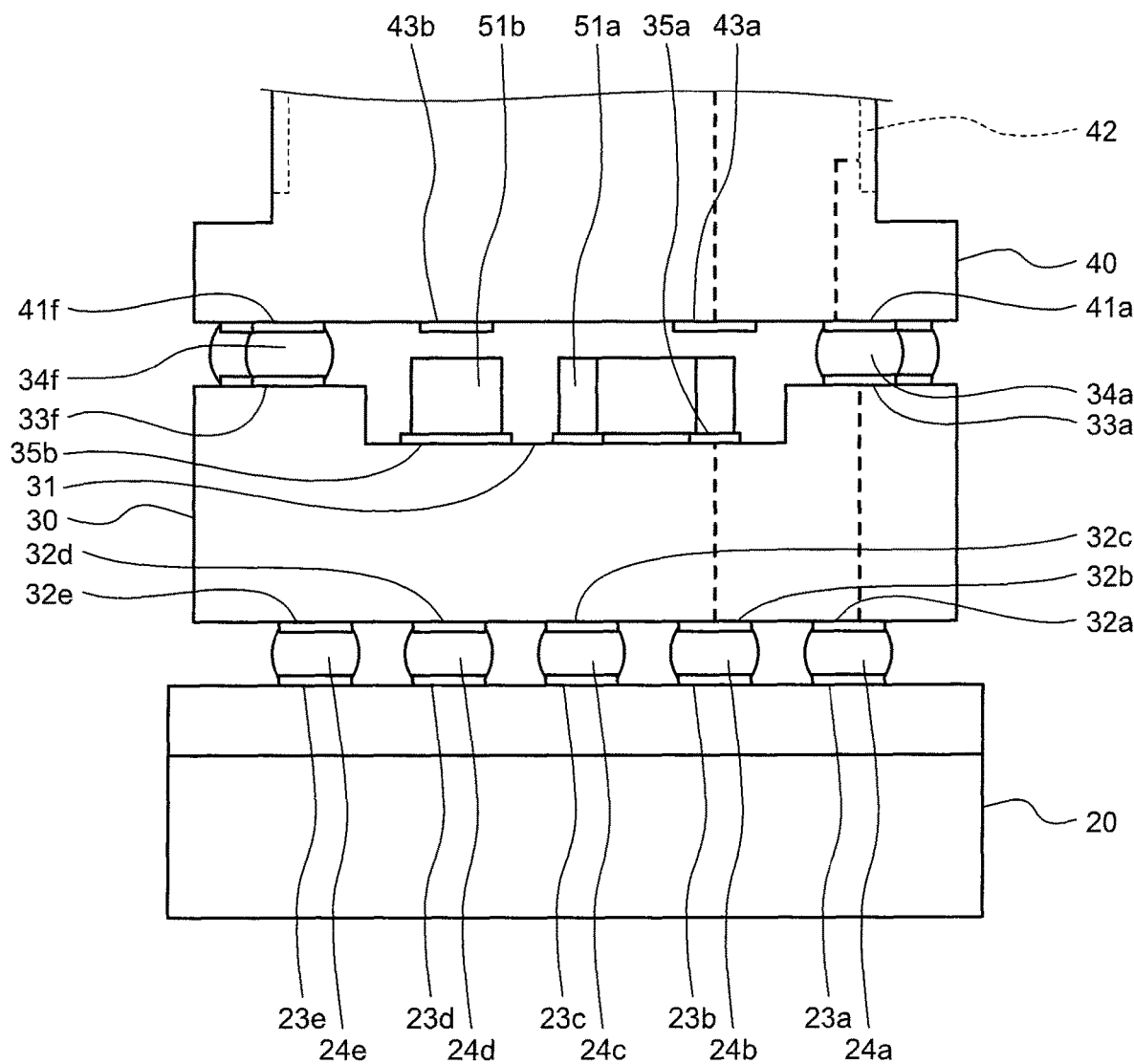
FIG. 9 is a partially enlarged view of an imaging unit of a comparative example.

In the following, arrangement positions of the electronic component 51 and the dummy pad 43, and wirings of each of the electrode pads, the mounting lands 35, and the dummy pads 43 will be described with reference to the drawings. FIG. 6 is a side view of the imaging unit 10 illustrated in FIG. 2. FIG. 7 is a partially enlarged view of the imaging unit 10 illustrated in FIG. 6. FIG. 8 is a partially enlarged view of the imaging unit 10 taken from a side surface side facing the surface illustrated in FIG. 7. FIG. 9 is a partially enlarged view of an imaging unit of a comparative example.

As illustrated in FIG. 6 and FIG. 7, when the dummy pad 43a is projected by parallel light in the optical axis direction (the direction orthogonal to the surface f4 and the surface f5 that are the connecting surfaces between the first circuit board 30 and the second circuit board 40), a shadow of the dummy pad 43a is disposed at the position overlapping the electrode located on the right side of the electronic component 51a in the drawings (FIG. 7).

A space h1 between the first circuit board 30 and the second circuit board 40 is designed such that the electronic component 51a and the dummy pad 43a (and the electronic component 51*e* and the dummy pad 43*b* (See, FIG. 8) are not in contact with each other and have a predetermined space h2. However, even when designing the electronic components 51*a* and the dummy pad 43*a* (and the electronic component 51*e* and the dummy pad 43*b*) so as to be separated at the distance of the space h2, due to variation in accuracy of the outer diameter of the connecting member 34, variation in pressure applied at the time of connection of the second electrode pad 33 and the third electrode pad 41, and variation in amount of soldering at the time of connection of the electronic component 51 and the mounting land 35, short circuits may be caused by the electronic component 51*a* and the dummy pad 43*a* (and/or the electronic component 51*e* and the dummy pad 43*b*) being in contact with each other at a certain rate, which is the cause of failure.

In the imaging unit in FIG. 9, as illustrated by dashed lines, the dummy pad 43*a* is connected to vias and wirings that do not reach the third electrode pads 41*a* and, furthermore, the mounting land 35*a* having mounted thereon an electronic component that is located at the position overlapping the dummy pad 43*a* when the dummy pad 43*a* is projected is connected to vias and wirings that do not reach the second electrode pad 33*a*. In contrast, in the embodiment according to the present disclosure, as illustrated by dashed lines in FIG. 7 and FIG. 8, the dummy pads 43*a* and 43*b* are connected to the third electrode pads 41*a* and 41*j*, respectively, and the mounting lands 35*a* and 35*e* are also connected to the second electrode pads 33*a* and 33*j*, respectively, by the vias and wirings inside the first circuit board 30. By arranging the wirings in this way, even if short circuits occur between the electronic components 51 and the dummy pads 43, it is possible to use the imaging unit 10 without affecting the performance of the imaging unit 10. Furthermore, because there is no need to increase the space h1 between the first circuit board 30 and the second circuit board 40 in order to avoid the electronic components 51 from being brought into contact with the dummy pads 43, the size of the imaging unit 10 can be reduced. Furthermore, it is preferable that a depth h3 of the concave portion 31 be smaller than a height h4 that is needed when the electronic components 51 are mounted on the mounting lands 35. By decreasing the depth h3 of the concave portion 31 than the height h4 needed when the electronic components 51 are mounted on the mounting lands 35, it is possible to set the space h2 between the electronic components 51 and the dummy pads 43 to a further smaller value.

Furthermore, it is preferable that the wirings that are connected to the dummy pad 43*a* and the dummy pad 43*b*, respectively, be power supply lines or ground lines and it is preferable that the electronic components 51*a* and 51*e* disposed at the positions overlapping the dummy pads 43*a* and 43*b*, respectively, be condensers or the like used to stably drive the semiconductor package 20.

In the imaging unit 10 according to the embodiment, because the mounting lands 35*a* and 35*e* having mounted thereon the electronic components 51*a* and 51*e* that are disposed at the location overlapping the dummy pads 43*a* and 43*b* at the time of projection are connected to the dummy pads 43*a* and 43*b* that are connected to the third electrode pads 41*a* and 41*j*, respectively, by the vias and the wirings; are connected to the connecting members 34*a* and 34*j*; are connected to the second electrode pads 33*a* and 33*j*; and are connected by the vias and the wirings, even if the space h1 between the first circuit board 30 and the second circuit board 40 are decreased, it is possible to reduce the rate of occurrence of failure.

Furthermore, in the embodiment, because the electronic components 51 and the cables 60 are mounted on the first circuit board 30 and the second circuit board 40, respectively. Because the electronic components 51 are mounted on the first circuit board 30 disposed in the vicinity of the image sensor 21, it is possible to decrease the impedance between the image sensor 21 and the electronic components 51. Furthermore, by accommodating the electronic components 51 in the concave portion 31 formed on the surface f4 that is the back surface of the first circuit board 30, it is possible to shorten the length of the hard portion of the imaging unit 10 in the optical axis direction.

Furthermore, because the first circuit board 30, the second circuit board 40, and the cables 60 are formed within the plane of projection of the semiconductor package 20 in the optical axis direction, the size of the imaging unit 10 can be reduced. Furthermore, regarding the first circuit board 30 and the second circuit board 40, because connection to the semiconductor package 20 and connection of the first circuit board 30 to the second circuit board 40 are performed on the surface f3, the surface f4, the surface f5 that are the surfaces parallel to the laminated board surface on which fine pitch wirings can be arranged, it is possible to obtain the small sized and highly reliable imaging unit 10.

Figure 10:
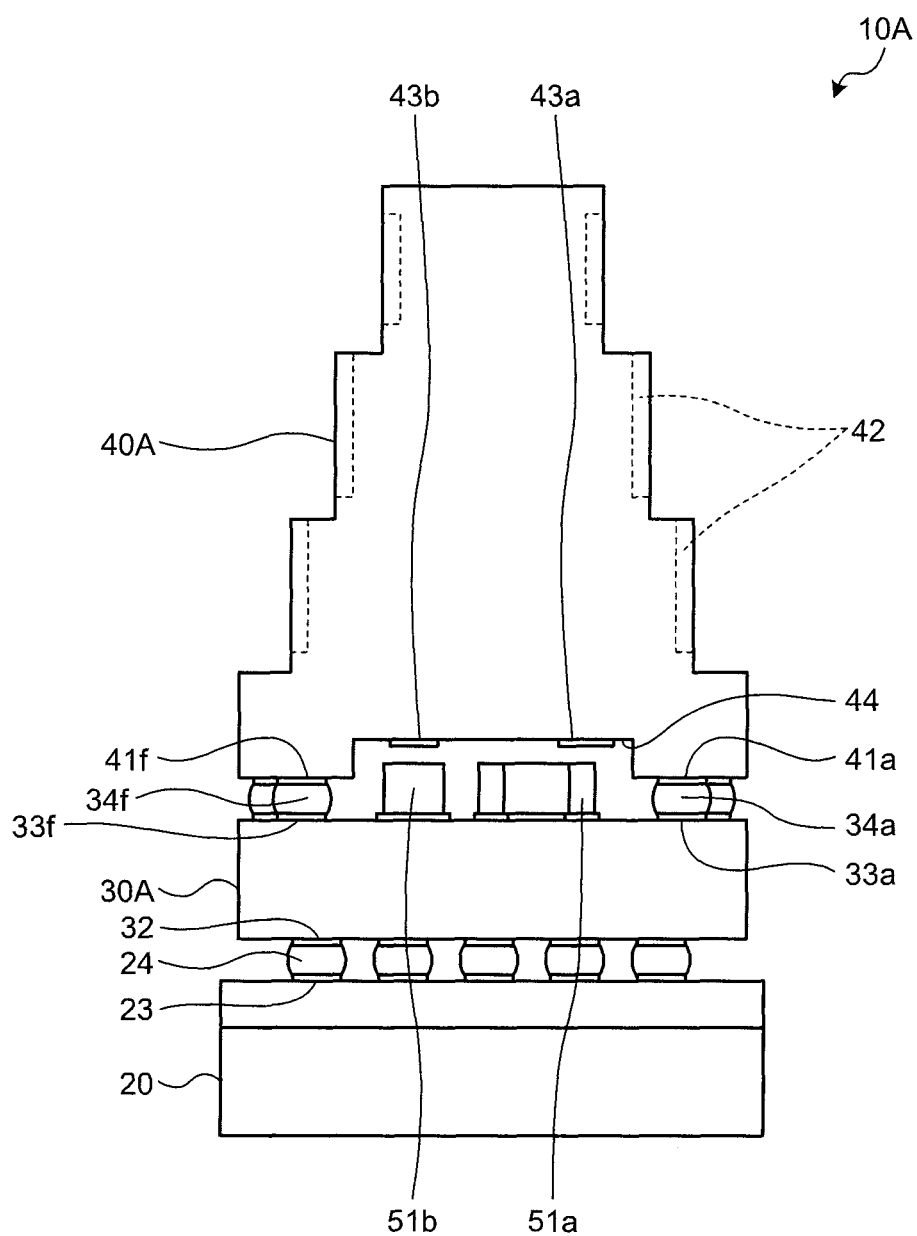
FIG. 10 is a side view of an imaging unit according to a modification of the embodiment of the present disclosure.
Figure 11:
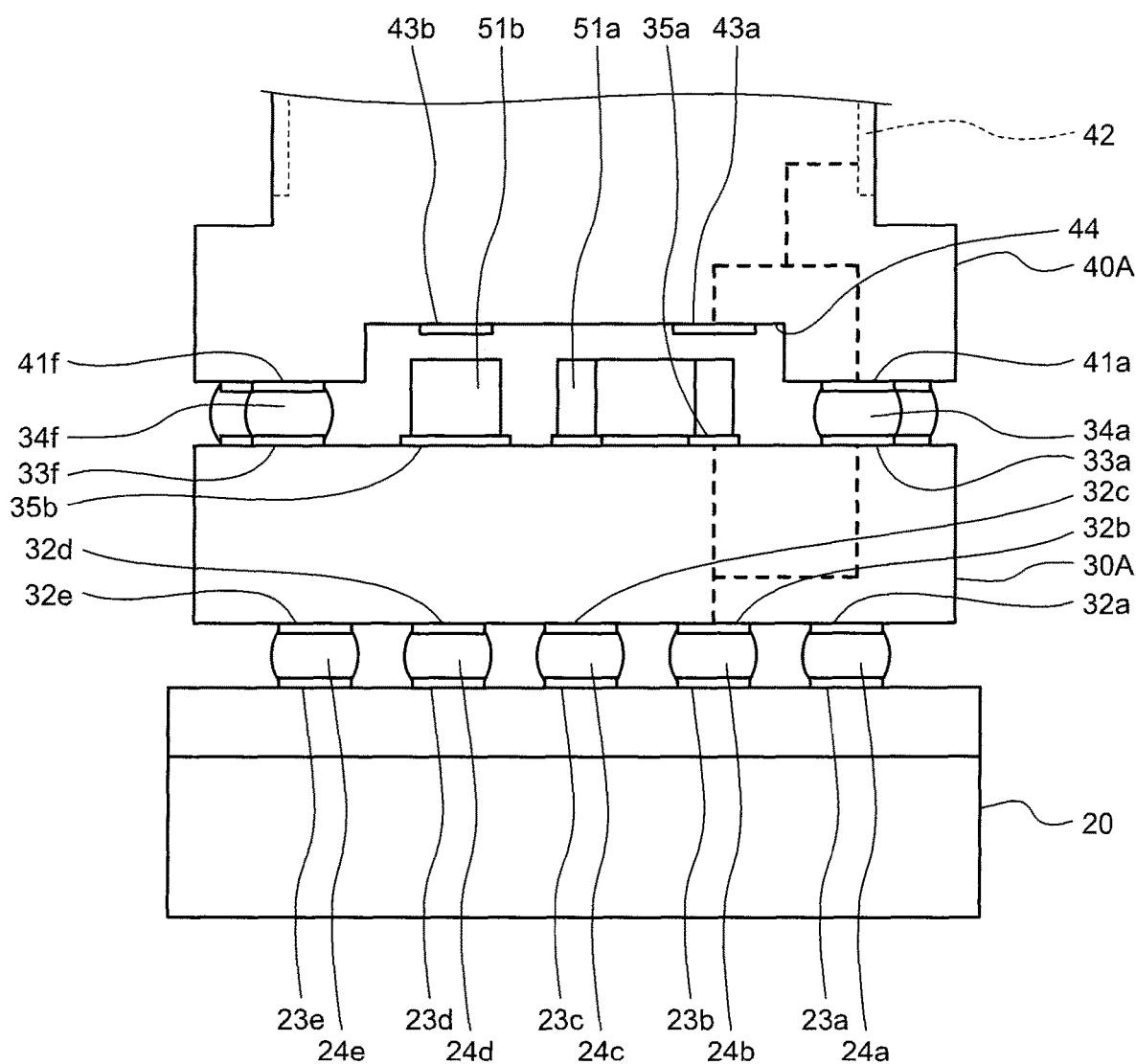
FIG. 11 is a partially enlarged view of the imaging unit illustrated in FIG. 10.

Furthermore, in the embodiment described above, because the concave portion 31 is provided on the surface f4 that is the back surface of the first circuit board 30; however, the concave portion may also be provided on the surface f5 that is the front surface of the second circuit board. FIG. 10 is a side view of an imaging unit 10A according to a modification of the embodiment of the present disclosure. FIG. 11 is a partially enlarged view of the imaging unit 10A illustrated in FIG. 10.

In the imaging unit 10A, the first electrode pads 32 are formed on the surface f3 of a first circuit board 30A and are electrically and mechanically connected to the sensor electrodes 23 on the semiconductor package 20 via the connecting members 24. Furthermore, at the center portion of the surface f4 of the first circuit board 30A, the mounting lands 35*a* to 35*e* (35) on which the electronic components 51*a* to 51*e* are mounted and the second electrode pads 33*a* to 33*j* are formed.

At the center portion of the surface f5 that is the front surface of a second circuit board 40A, the concave portion 44 is provided and the dummy pads 43*a* and 43*b* are formed in the concave portion 44. The third electrode pads 41*a* to 41*j* are formed at the portions other than the concave portion 44 on the surface f5 of the second circuit board 40A and are electrically and mechanically connected to the second electrode pads 33*a* to 33*j* on the surface f4 of the first circuit board 30A via the connecting members 34*a* to 34*j*.

The dummy pads 43*a* and 43*b* are disposed, similarly to the embodiment, so as to be rotationally symmetric with respect to the center C of the front surface of the surface f5. The dummy pad 43*a* is disposed at the position overlapping the electrode located on the right side of the electronic component 51*a* in the drawing, whereas the dummy pad 43*b* is disposed at the position overlapping the electrode located on the upper side of the electronic component 51*e* in the drawing (See FIG. 4).

In the imaging unit 10A according to the modification, similarly to the embodiment, by mounting the electronic components 51*a* to 51*e* around the center of the first circuit board 30A, it is possible to stably drive the image sensor 21 and thus obtain high quality images. Furthermore, by providing the concave portion 44 on the surface f5 of the second circuit board 40A and accommodating the electronic components 51a to 51e, it is possible to shorten the length of the hard portion of the imaging unit 10A in the optical axis direction.

Furthermore, in the imaging unit 10A, because the mounting lands 35a and 35e having mounted thereon the electronic components 51a and 51e that are disposed at the location overlapping the dummy pads 43a and 43b are connected to the dummy pads 43a and 43b that are connected to the third electrode pads 41a and 41j, respectively, by the vias and the wirings; are connected to the connecting members 34a and 34j, are connected to the second electrode pads 33a and 33j; and are connected by the vias and the wirings, even if the space h1 between the first circuit board 30A and the second circuit board 40A are decreased, it is possible to reduce the rate of occurrence of failure.

Furthermore, depending on the size of the electronic components 51 and the connecting members 34, the concave portion 31 of the surface f4 that is the back surface of the first circuit board 30 and the concave portion 44 of the surface f5 that is the front surface of the second circuit board 40A are not always needed to be formed.

According to the present disclosure, by connecting, by using connecting members, second electrode pads, wirings, or the like, mounting lands for electronic components overlapping, at the time of projection, dummy pads that are used as alignment marks to the dummy pads that are connected to third electrode pads by wirings or the like, it is possible to implement a reduction in size and avoid failure of the electronic components due to short circuits even when the dummy pads are in contact with the electronic components.

What is claimed is:

1. An electronic circuit unit comprising:
   a first circuit board in which a plurality of first electrode pads are formed on a first front surface and a plurality of mounting lands and a plurality of second electrode pads are formed on a first back surface, the first circuit board including a first plurality of vias and wirings;
   a second circuit board in which dummy pads and a plurality of third electrode pads that are connected to corresponding ones of the second electrode pads on the first circuit board via first connecting members are formed on a second front surface of the second circuit board and that has a second plurality of vias and wirings; and
   a plurality of electronic components that are connected to the mounting lands, wherein
   at least part of the dummy pads oppose at least part of electrodes of one of the plurality of electronic components, and
   the mounting lands connected to the electronic components that oppose the at least part of the dummy pads are electrically connected to the dummy pads through a predetermined path, wherein
   the predetermined path includes
      the first plurality of vias and the wirings of the first circuit board that connect the plurality of mounting lands and the second electrode pads,
      the second plurality of vias and the wirings of the second circuit board that connect the third electrode pads and the dummy pads, and
      the first connecting members that connect the second electrode pads and the third electrode pads, respectively.

2. The electronic circuit unit according to claim 1, wherein
   a concave portion is formed on the first back surface of the first circuit board, and
   the plurality of electronic components are mounted on the plurality of mounting lands that are formed in the concave portion of the first circuit board.

3. The electronic circuit unit according to claim 1, wherein
   a concave portion is formed on the second front surface of the second circuit board, and
   the plurality of electronic components mounted on the first circuit board are accommodated in the concave portion of the second circuit board.

4. The electronic circuit unit according to claim 1, wherein
   the second plurality of vias and the wirings to which the dummy pads are connected are power supply lines or ground lines, and
   the electronic components opposed to the dummy pads are condensers.

5. The electronic circuit unit according to claim 1, wherein the dummy pads are located at rotationally symmetric positions with respect to a center of the second front surface of the second circuit board and serve as alignment marks.

6. An imaging unit comprising:
   an electronic circuit unit according to claim 1; and
   a semiconductor package comprising an image sensor provided on a third front surface of the semiconductor package, and sensor electrodes formed on a second back surface of the semiconductor package, wherein
   first electrode pads included in the electronic circuit unit are connected to the respective sensor electrodes included in the semiconductor package via second connecting members, and
   the electronic circuit unit is located within a plane of projection of the semiconductor package in an optical axis direction of the semiconductor package.

7. An endoscope comprising:
   an insertion portion; and
   the imaging unit according to claim 6 provided at a distal end of the insertion portion.

8. An imaging module comprising:
   an electronic circuit unit according to claim 1;
   a semiconductor package comprising an image sensor provided on a third front surface of the semiconductor package, and electrodes formed on a second back surface of the semiconductor package; and
   a plurality of cables, wherein
   cable connection electrodes are formed on two opposing side surfaces of the second circuit board in the electronic circuit unit and the plurality of cables are connected to corresponding one of the cable connection electrodes,
   first electrode pads included in the electronic circuit unit are connected to the respective sensor electrodes included in the semiconductor package via second connecting members, and
   the electronic circuit unit and the plurality of cables are located within a plane of projection of the semiconductor package in an optical axis direction of the semiconductor package.

9. An endoscope comprising:
   an insertion portion; and
   the imaging module according to claim 8 provided at a distal end of the insertion portion.

* * * * *